United States Patent [19]

Nussbaumer et al.

[11] Patent Number: 4,490,256
[45] Date of Patent: Dec. 25, 1984

[54] APPARATUS FOR STATIC MEMBRANE FILTRATION

[75] Inventors: Dietmar Nussbaumer; Horst Perl; Khuong T. Vinh, all of Göttingen, Fed. Rep. of Germany

[73] Assignee: Sartorius GmbH, Göttingen, Fed. Rep. of Germany

[21] Appl. No.: 554,995

[22] Filed: Nov. 25, 1983

[30] Foreign Application Priority Data

Nov. 26, 1982 [DE] Fed. Rep. of Germany ....... 3243862

[51] Int. Cl.$^3$ .............................................. B01D 33/00
[52] U.S. Cl. ..................................... 210/359; 210/927
[58] Field of Search ............... 210/359, 927, 516, 517, 210/518, 117, DIG. 24, 781, 782, 789

[56] References Cited

U.S. PATENT DOCUMENTS

| | | | |
|---|---|---|---|
| 3,512,940 | 5/1970 | Shapiro | 210/359 |
| 3,870,639 | 3/1975 | Moore et al. | 210/359 |
| 3,894,950 | 7/1975 | Ayres et al. | 210/516 |
| 3,894,951 | 7/1975 | Ayres | 210/516 |
| 3,897,337 | 7/1975 | Ayres | 210/516 |
| 3,931,010 | 1/1976 | Ayres et al. | 210/516 |
| 3,962,085 | 6/1976 | Liston et al. | 210/131 |
| 4,021,352 | 5/1977 | Sarstedt | 210/789 |
| 4,154,690 | 5/1979 | Ballies | 210/516 |
| 4,202,769 | 5/1980 | Greenspan | 210/516 |

Primary Examiner—John Adee
Attorney, Agent, or Firm—Balogh, Osann, Kramer, Dvorak, Genova & Traub

[57] ABSTRACT

An apparatus for static membrane filtration, including a cylindrical sample vessel containing a filtration medium and subjected to centrifugal acceleration. A plunger is mounted in sealed manner in the sample vessel, and is being movable therein. An asymmetrical membrane is attached at the end of the plunger facing the bottom of the sample vessel, with the filtration active side of the membrane facing towards the outside. The bottom of the sample vessel is provided with a sealable opening. The mean density of the plunger is greater than the density of the filtration medium, and the length of the plunger in cm is greater or equal to the reciprocal of the mean plunger density in g/cm$^3$ reduced by 1.

11 Claims, 4 Drawing Figures

APPARATUS FOR STATIC MEMBRANE FILTRATION

The invention relates to an apparatus for static membrane filtration including a cylindrical sample vessel containing the filtration medium and subjected to the centrifugal acceleration.

Static membrane filtration is the simplest filtration method. In it, the medium to be filtered is in contact under an excess pressure with the membrane without forced flows. It can be employed successfully when only very small substance amounts need be deposited from the suspension or solution, for example recovering sterile filtrates from weakly germinated solutions.

To avoid disadvantages of static filtration tangential overflow has already been employed but because of the large apparatus expenditure, it has not been able to establish itself (any more than agitating cells) when small sample amounts and/or mechanically sensitive substances are to be filtered.

The invention is based on the problem of avoiding falsifications in the concentrating. This applies in particular when extracting extremely small concentrate volumes of the order of magnitude of 50 μl, and the intention is to permit execution of the filtration in a centrifuge.

This is achieved with an apparatus of the type mentioned at the beginning by a plunger or piston which is movable in the sample vessel, carries at the end face or face facing the vessel bottom a membrane and is mounted in laterally sealed manner in the cylindrical vessel; and by a sealable opening in the bottom of the sample vessel.

Preferably, as driving force of the filtration the piston or plunger movement in a centrifuge is utilized, the plunger having a higher density than the filtration medium and the length $l_K$ of the plunger fulfilling the following condition:

$$l_K \geq \frac{1}{\rho_K - \rho_{fl}}$$

$l_K$ = length of the plunger (cm) with cylindrical plunger shape (with plungers which are not cylindrical $l_K$ is the length which a cylinder would have of the same solid volume and same cross-section area)

$\rho_K$ = mean density of the plunger (g/cm$^3$) (plunger mass divided by solid volume)

$\rho_{fl}$ = density of the fluid or liquid to be filtered (g/cm$^3$). (may be put equal to 1)

The range of the plunger length is advantageously 0.5 to 2.5 cm and that of the mean plunger density correspondingly at least 1.4 to 3 g/cm$^3$. Preferred materials are thermoplastics suitable for injection molding which have been brought to the desired mean density by an insertion of special steel.

Plungers or pistons which fulfil the aforementioned condition exert in the immersed state on a liquid disposed therebelow a hydrostatic pressure of at least 10 mm water column which corresponds in a centrifuge at a relative centrifugal acceleration of for example 2000 g to a pressure of 2 bar.

It is advantageous if the centrifugal acceleration seen from the liquid to be filtered has no vector in the direction of the membrane.

Preferably, the mean density of the plunger is greater than the density of the medium to be filtered, for example. The length of the plunger in cm is greater or equal to the reciprocal of the mean plunger density in g/cm$^3$ reduced by 1.

In particular, the mean plunger density is more than 1.4 g/cm$^3$ and great constructional advantages are obtained by a plunger which is preferably made from a thermoplastic plastic with an insert of special steel.

According to a particular embodiment of the invention the membrane is an asymmetric ultrafiltration membrane and adhered in sealed manner to the end of the plunger facing the bottom of the sample vessel with the filtration active side of the membrane towards the outside.

The apparatus can be used both for recovering concentrate and for recovering filtrate. The main field of use is the quantitative recovery of minute concentrate amounts from diluted protein solutions.

The feature of simple apparatus in the invention is of significance in particular in the production of one-way apparatuses.

The static filtration is thus utilized in the acceleration field of a centrifuge in that a deliberately intended appreciable hydrostatic pressure difference is produced and employed for the purposes of the invention.

Although with known apparatuses the centrifugal acceleration is utilized to produce an effective hydrostatic pressure difference, with the novel arrangement in the subject of the application the depositing of depositable constituents present on the membrane is avoided and it is also avoided that the concentrate formed, which generally has a higher density than the starting solution, can accumulate on the membrane.

Examples of embodiment of the invention will be explained hereinafter with the aid of the attached drawings, wherein.

Figure 2:
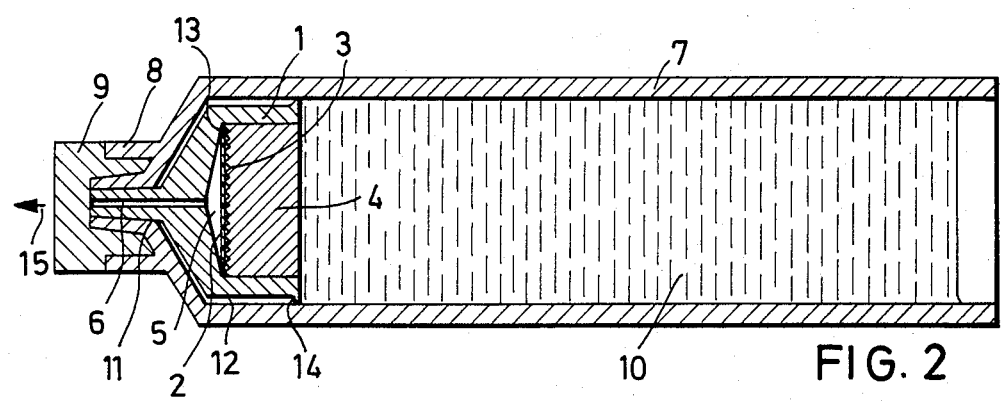
FIGS. 2 to 4 show a further embodiment intended for extremely small concentrate volumes.
Figure 3:
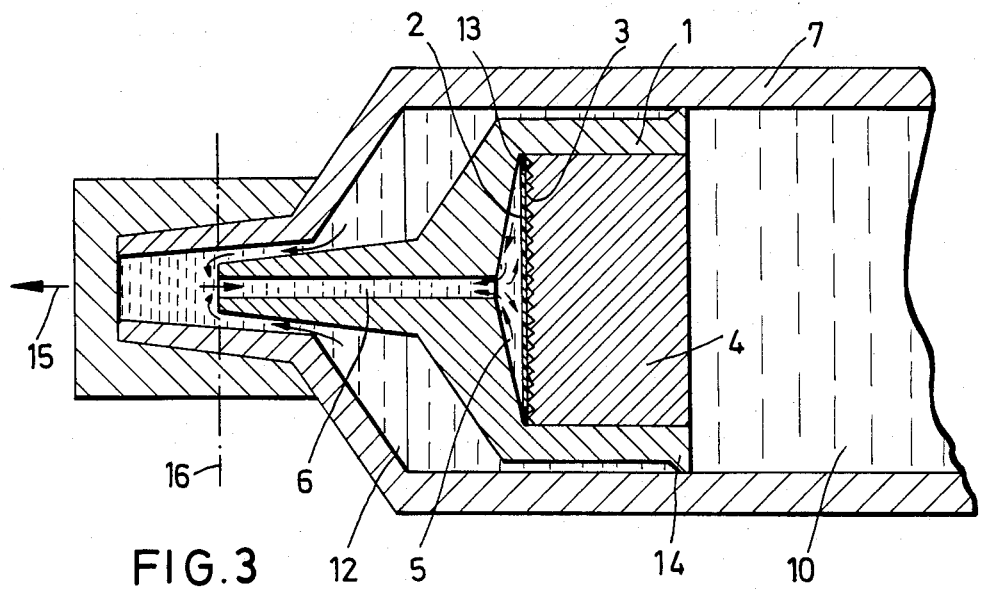
Figure 4:
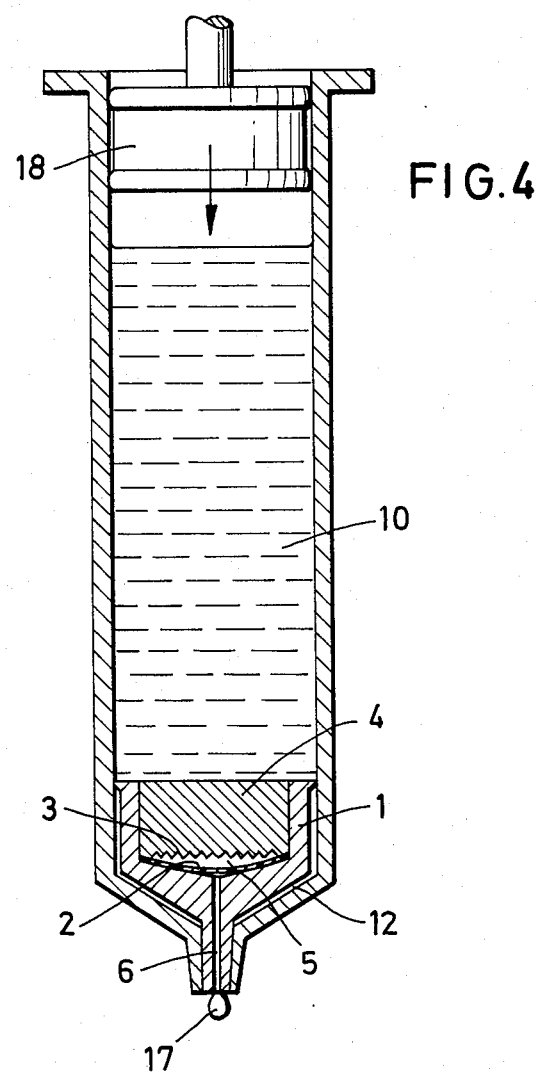

Referring to FIGS. 2-4, the plunger 1 consists of a material of higher density than the rinsing liquid and is disposed laterally at 14 in a tube 7 with detachable tip. This embodiment is particularly suitable both for the recovery of protein concentrates and of filtrate from protein solutions of any concentration.

The embodiment of FIGS. 2 to 4 is used when extremely small concentrate volumes are to be recovered from very diluted silutions. It is used for example in a conventional injection syringe. In the Figures the same components are designated with the same reference numerals.

Figure 1:
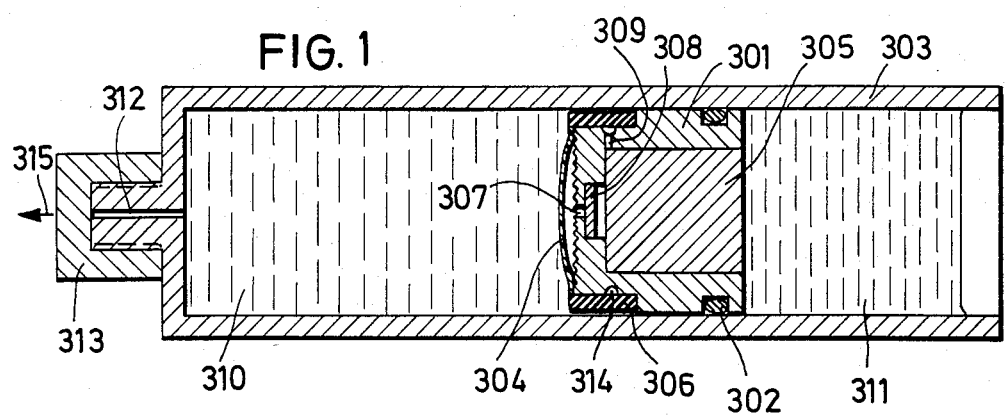
FIG. 1 shows a first embodiment of the invention intended in particular for the recovery of protein concentrates or filtrate.

Referring to FIG. 1, the plunger 301 has a special steel core 305 for increasing the mean density and thus the filtration-active pressure difference. The core is only pressed into the plunger so that the filtrate can flow through the remaining unsealed area and into the filtrate space 311. The plunger 301 is mounted in the sample vessel 303 in a sealed manner by an O-ring seal 302.

The essence of this plunger design is that to expel the concentrate after termination of the filtration air can be forced through in the reverse direction when the filtrate has been poured off. The air is injected with a conventional syringe plunger. The valve 308 closes the filtrate bore 307. The air flows through the bore 309 into the annular groove 314, inflates the flexible tube 306 attached as valve and when the screw cap 313 is removed it forces the concentrate disposed in the tip 312 into the open. The valve 306 is used for the purpose of blasting air from the top to the bottom so as to facilitate the expulsion of the concentrate.

In spite of widespread use, this design meets its limits when concentrate volumes of less than 100 μl are to be achieved. The reason is that a major part of the unconcentrated starting solution disposed in the dead volume adjacent the plunger is blown out as well and subsequently dilutes the concentrate formed.

The embodiment of FIGS. 2 to 4 is employed when extremely small concentrate volumes are to be recovered from highly dilute solutions. It is used for example in a commercial conventional injection syringe.

FIG. 2 shows the apparatus after completion of the filtration at the lower dead point. The plunger body 1 is adapted as exactly as possible to the conical end of the syringe. The gap 12 which is nevertheless present has been exaggerated in size for clarification. The conical extension of the plunger body is located in the end position in sealing manner in the likewise inwardly conical tip of the syringe. This is possible because the material from which the syringe is made (polyethylene) has a certain elasticity. The liquid disposed in the gap 12 and consisting for reasons still to be explained of unconcentrated starting solution thus cannot emerge and dilute the concentrate on removal of the latter. If the concentrate were disposed in the gap unacceptable protein losses would occur. Since however starting solution is involved and the volume is small compared with the initial volume, the losses are negligible.

The membrane 2 is connected by the weld seam 13 from the inside to the plunger body 1 with the filtration-active layer. Placed on the membrane are the filter support 3 and the special steel core 4. The filter support 3 can in the simplest case be a fabric disc of corresponding compression strength. As in the previous example the special steel core is pressed in loosely so that the filtrate can flow past the core into the filtrate space 10. Beneath the membrane there is a flatly conical space 5 which opens into the bore 6 of the conical extension. The volumes of 5 and 6 define together the attainable concentrate volume. 9 is the sealing cap which is inserted into the lower connection 8 of the injection syringe. The nature of the plunger seal 14, shown here in the form of a sealing lip, is not essential to the invention. An O-ring seal could for example also be used.

For the filling, the filtration plunger is first pushed with a conventional syringe plunger into the lower dead center position whereupon the syringe is filled in the usual manner by pulling up the plunger. After removing the air and sealing the tip the centrifuging operation is carried out.

The principle of the function is apparent from FIG. 3. It is assumed that the dead volume and wetted areas of plunger and syringe cannot be minimized to any desired extent because of constructional, production-technical, and other reasons (e.g. bulging under the hydrostatic pressure). Steps are therefore taken to ensure that at the end of the filtration no concentrate but unconcentrated starting solution is in the dead volume and in contact with most wetted surfaces.

When the piston moves in the course of the filtration in the direction of the syringe tip concentrated solution can always only be located "beneath" the opening of the conical extension (left of the line 16 in FIG. 3) because concentrate can emerge from the plunger interior only at this point and because of the higher density convection of concentrate is possible only in the direction of the centrifugal acceleration. Thus, the moving plunger therefore pushes in front of itself between the seal 14 and the opening an initially constant volume 12 of the starting solution. In the course of its movement, this volume element gradually comes into areas in which there has previously been solution already concentrated to various degrees. The inner walls of the syringe are therefore "washed" by the starting solution.

FIG. 3 illustrates the phase in which the conical extension dips into the syringe tip in which the concentrate formed so far has collected. Since the time at which the plunger opening entered the conical region of the syringe the volume 12 has diminished. This continues to happen to an intensified extent and the starting solution disposed in the decreasing volume element 12 is thereby forced to flow into the syringe tip and from there into the opening of the plunger. As a result, this part of the syringe wall, which was in contact with the previously most concentrated solution, is rinsed particularly intensively with the starting solution. This operation is concluded when the conical plunger extension by contact with the inner wall of the syringe tip seals the dead volume 12 (remainder of the starting solution) with respect to the concentrate space (condition according to FIG. 2).

In FIG. 3 convection of flows presumably occurring in the interior of the plunger body 1 are also indicated. It is important that not only the entry of the starting solution takes place through the opening at the tip but at the same time also the emergence of already formed concentrate. Certainly, there is a lower limit for the diameter of the bore 6 at which this is no longer possible. With the order of magnitude of about 1 mm in question here this has obviously not yet been reached. From the point of view of the filtration rate the emergence of concentrate is certainly desired because it delays the protein enrichment in the interior of the plunger, which leads to a reduction of the filtration rate.

FIG. 4 shows the removal of the concentrate. After removing the closure member 9 the syringe plunger 18 is again introduced from above. The pressure exerted by the plunger on the air space effects initially that due to its elasticity the membrane 2 is lifted off the filter support 3 and pressed against the wall of the flatly conical cavity 5, a corresponding volume of concentrate 17 thereby emerging at the bottom. The further maintenance of the excess pressure on the filtrate side leads to filtrate passing through the membrane opposite to the filtration direction and expelling the residual concentrate from the volumes 5 and 6.

The further procedure depends on the purpose of the concentrating operation. If primarily an exactly defined concentrating ratio and/or a high protein concentration is necessary, the amount of concentrate removed is only such that a dilution by following filtrate is impossible. This will be the case generally in the concentration for electrophoretic separations. If however a maximum possible recovery of the protein used is important, for example in micropreparative work, the rinsing will be carried out with correspondingly more filtrate.

We claim:
1. Apparatus for static membrane filtration, including a cylindrical sample vessel containing a filtration medium and subjected to centrifugal acceleration, the apparatus comprising a plunger mounted in sealed manner in the sample vessel and being movable therein, and an asymmetrical membrane attached to said plunger at an end thereof facing the bottom of the sample vessel, the membrane being adhered to said plunger in sealed manner and having its filtration active side towards the outside, the sample vessel having a sealable opening in the bottom thereof, the mean density of said plunger being greater than the density of the filtration medium, and the length of said plunger in cm being greater or equal to the reciprocal reduced by 1 of the mean plunger density in g/cm$^3$.

2. Apparatus according to claim 1, wherein the mean plunger density is greater than 1.4 g/cm$^3$.

3. Apparatus according to claim 1, wherein said plunger consists of a thermoplastic with an insert of steel.

4. Apparatus according to claim 1, wherein the filtration medium is disposed between the bottom of the sample vessel and said plunger carrying the membrane.

5. Apparatus according to claim 1, wherein the centrifugal acceleration respective to the filtration medium has no vector in the direction of the membrane.

6. Apparatus according to claim 1, wherein the filtration medium consists of water.

7. Apparatus according to claim 4, wherein said plunger further comprises a flatly conical space disposed beneath the membrane, and a conical extension having a bore which is disposed centrally with respect to the flatly conical space and leads outwardly therefrom.

8. Apparatus according to claim 7, wherein said plunger has a body corresponding in shape to the conical end of a syringe.

9. Apparatus according to claim 7, wherein the filtration active side of the membrane is connected by a weld seam to the inner bottom of said plunger and the filtrate side of the membrane is covered by a filter support and a steel core.

10. Apparatus according to claim 1, further comprising a valve formed as an inflatable hose section around said plunger.

11. Apparatus according to claim 1, wherein the apparatus is used for the quantitative recovery of minute concentrate amounts from diluted protein solutions.

* * * * *